(12) United States Patent
Sukegawa

(10) Patent No.: US 8,092,442 B2
(45) Date of Patent: Jan. 10, 2012

(54) ABSORBING ARTICLE

(75) Inventor: Hiroto Sukegawa, Sakura (JP)

(73) Assignee: Daio Paper Corporation, Ehime (JP)

( * ) Notice: Subject to any disclaimer, the term of this patent is extended or adjusted under 35 U.S.C. 154(b) by 0 days.

(21) Appl. No.: 12/934,709

(22) PCT Filed: Mar. 26, 2009

(86) PCT No.: PCT/JP2009/056125
§ 371 (c)(1), (2), (4) Date: Sep. 27, 2010

(87) PCT Pub. No.: WO2009/119740
PCT Pub. Date: Oct. 1, 2009

(65) Prior Publication Data
US 2011/0015603 A1 Jan. 20, 2011

(30) Foreign Application Priority Data

Mar. 28, 2008 (JP) .................................. 2008-087910

(51) Int. Cl.
*A61F 13/15* (2006.01)
(52) U.S. Cl. ........ 604/393; 604/398; 604/397; 604/400; 604/385.14; 604/385.19
(58) Field of Classification Search .................. 604/393, 604/398, 397, 400, 385.14, 385.19
See application file for complete search history.

(56) References Cited

U.S. PATENT DOCUMENTS 5,383,867 A * 1/1995 Klinger .................... 604/385.23
5,843,065 A * 12/1998 Wyant ...................... 604/385.09

(Continued)

FOREIGN PATENT DOCUMENTS

EP 2 027 840 A1 2/2009

(Continued)

OTHER PUBLICATIONS

International Search Report dated Jun. 23, 2009 issued in International Appln. No. PCT/JP2009/056125.

(Continued)

*Primary Examiner* — Jacqueline F Stephens
(74) *Attorney, Agent, or Firm* — Holtz, Holtz, Goodman & Chick, PC

(57) ABSTRACT

A pants type absorbing article (10) comprises an absorbing body (3) including an absorber (30), and an enclosure (2) equipped with a ventral portion (2a), a dorsal portion (2b) and a portion (2c) from the crotch to the cuff located therebetween and makes the absorbing body (3) adhere to the portion (2c) from the crotch to the cuff, wherein the enclosure (2) is provided, at a lower part of the ventral portion (2a), with an opening (5) having a cut (50) along the width direction and opening when the upper and lower parts of the cut (50) are pulled in the direction separating from each other, the absorbing body (3) is arranged across the opening (5) from the portion (2c) from the crotch to the cuff to the ventral portion (2a) of the enclosure (2) in the longitudinal direction, the portion below the opening (5) constitutes an adhering portion (3B) of the absorbing body (3) and the enclosure (2), the portion above the opening (5) constitutes a non-adhering portion (3A) of the absorbing body (3) and the enclosure (2), and a means (6) for fixing the absorbing body (3) and the enclosure (2) removably at the non-adhering portion (3A) is provided. Consequently, closed state of the opening can be maintained.

10 Claims, 9 Drawing Sheets

U.S. PATENT DOCUMENTS

2003/0199844 A1 * 10/2003 LaVon et al. ............. 604/385.14
2007/0293841 A1    12/2007 Sasayama

FOREIGN PATENT DOCUMENTS

| | | |
|---|---|---|
| JP | 11-43802 A | 2/1999 |
| JP | 11-335903 A | 12/1999 |
| JP | 2007-330543 A | 12/2007 |
| JP | 2008-54987 A | 3/2008 |

OTHER PUBLICATIONS

Extended European Search Report (EESR) dated Mar. 28, 2011 (in English) in counterpart European Application No. 09723920.6.

* cited by examiner

ABSORBING ARTICLE

This application is a U.S. National Phase Application under 35 USC 371 of International Application PCT/JP2009/056125 filed Mar. 26, 2009.

TECHNICAL FIELD

The present invention relates to an absorbing article.

BACKGROUND ART

Conventionally, absorbing articles as represented by a disposable paper diaper are known. As for the disposable paper diaper, a pants type paper diaper and a tape type paper diaper are generally known.

Among the above, the pants type paper diaper (hereinafter, called paper diaper) includes an absorbing body in which an absorber is enclosed and an external body to which the absorbing body is fixed to. In view of leakage prevention, the external body is structured so as to closely contact the body of a wearer. Particularly, in the paper diaper for men, the external body does not have an opening or the like for urination from which the male genitalia is taken out, such as usually provided in male underwear. Therefore, it is difficult to urinate by himself.

Therefore, there is suggested a paper diaper in which an opening for taking out the male genitalia is provided in a ventral side of the paper diaper (for example, see Patent Document 1).
Patent Document 1: JP 2007-330543

DISCLOSURE OF THE INVENTION

Problem to be Solved by the Invention

However, because the opening formed in the paper diaper described in Patent Document 1 is a cut along the width direction, there is a problem that the opening opens when urination is carried out in the paper diaper due to the paper diaper sagging with the weight of the urine.

An object of the present invention is to provide an absorbing article which can maintain a closed state of an opening.

Means for Solving the Problem

In order to solve the above problem, according to a first aspect of the invention a pants type absorbing article is provided which includes an absorbing body including an absorber, a ventral portion, a dorsal portion, a crotch portion which is positioned between the ventral portion and the dorsal portion, and an external body for adhesively securing the absorbing body to the crotch portion. The external body has a cut along a width direction below the ventral portion and includes an opening which opens by pulling an upper part and a lower part of the cut so as to separate from each other. The absorbing body is positioned along a longitudinal direction from the crotch portion to the ventral portion of the external body going over the opening. A portion of the absorbing body below the opening forms an adhering portion where the absorbing body and the external body are adhered, and a portion of the absorbing body above the opening forms a non-adhering portion where the absorbing body and the external body are not adhered. And the absorbing article includes a fastening unit to detachably fasten the absorbing body and the external body at the non-adhering portion.

According to a second aspect of the invention, in the absorbing article of the first aspect the cut has a curved shape convexing upward.

According to a third aspect of the invention, in the absorbing article according to the first or second aspects, the opening includes holes provided at both ends of the cut so as to continue from the cut.

According to a fourth aspect of the invention, in the absorbing article according to any one of the first to third aspects, the opening includes a second cut which is formed to extend downward from a center of the cut so as to be orthogonal to the cut.

According to a fifth aspect of the invention, in the absorbing article according to any one of the first to fourth aspects, a width of the non-adhering portion of the absorbing body is narrower than a width of the opening.

According to a sixth aspect of the invention, in the absorbing article according to any one of the first to fifth aspects, an end portion of the non-adhering portion of the absorbing body is shaped in an arc shape.

According to a seventh aspect of the invention, in the absorbing article according to any one of the first to sixth aspects, at a boundary portion of the adhering portion and the non-adhering portion of the absorbing body, an embossing that continues along a width direction is carried out.

According to an eighth aspect of the invention, in the absorbing article according to any one of the first to sixth aspects, at a boundary portion of the adhering portion and the non-adhering portion of the absorbing body, a slit is formed along a width direction.

According to a ninth aspect of the invention, in the absorbing article according to any one of the first to eighth aspects, an elastic body in which a biasing force in a closing direction of the opening is given is provided in proximity to the opening.

According to a tenth aspect of the invention a pants type absorbing article is provided which includes an absorbing body including an absorber, a ventral portion, a dorsal portion, a crotch portion which is positioned between the ventral portion and the dorsal portion, and an external body for adhesively securing the absorbing body to the crotch portion. The external body includes an upper sheet for forming the ventral portion and a lower sheet for forming the dorsal portion and the crotch portion. A lower end portion of the upper sheet and an upper end portion of the lower sheet are overlapped so that the upper sheet is outside and the overlapped portion forms an opening which opens by pulling the lower end portion of the upper sheet and the upper end portion of the lower sheet so as to separate from each other. The absorbing body is positioned along a longitudinal direction from the crotch portion to the ventral portion of the external body going over the opening. A portion of the absorbing body below the opening forms an adhering portion where the absorbing body and the external body are adhered, and a portion of the absorbing body above the opening forms a non-adhering portion where the absorbing body and the external body are not adhered. And the absorbing article includes a fastening unit to detachably fasten the absorbing body and the external body at the non-adhering portion.

Effect of the Invention

According to the present invention, the absorbing body is positioned along the longitudinal direction going over the opening and the a portion of the absorbing body which positions in upper side than the opening is the non-adhering portion where this portion of the absorbing body does not adhere to the external body. Further, a fastening unit for detachably fastening the external body and the non-adhering portion is provided at the non-adhering portion.

Therefore, even when the entire absorbing article sags downward with the weight of urine when urination is carried out in the absorbing body, the upper part of the opening can be fastened by the fastening unit and the opening can be prevented from opening.

BEST MODE FOR CARRYING OUT THE INVENTION

Embodiment 1

Figure 1:
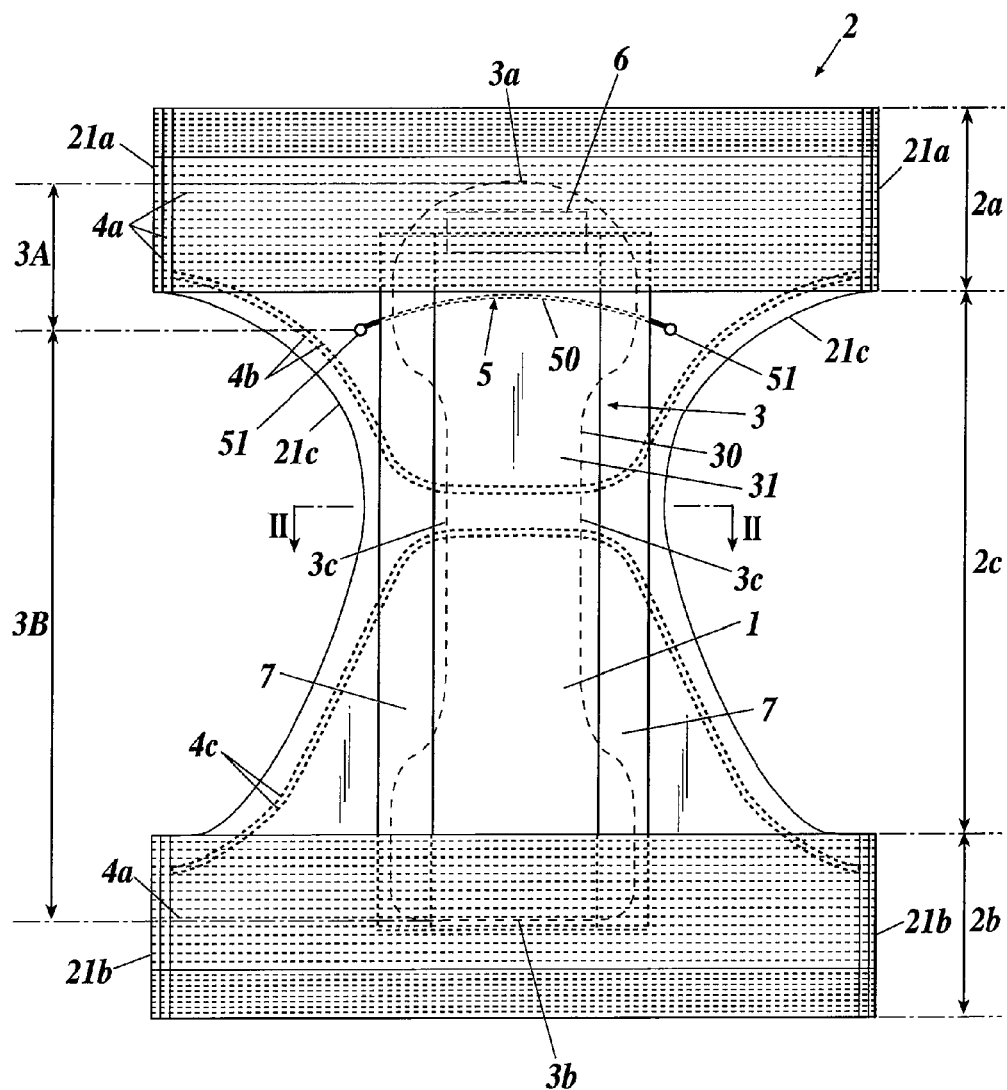
FIG. 1 This is a developed view of the paper diaper 10 of embodiment 1 in which the absorbing article of the present invention is applied.

Hereinafter, embodiment 1 of the present invention will be described with reference to the drawings. However, the scope of the invention is not limited to the examples shown in the drawings.

In the embodiment, description will be given by taking a pants type disposable paper diaper (hereinafter, called "paper diaper") as an absorbing article as an example.

Figure 2:
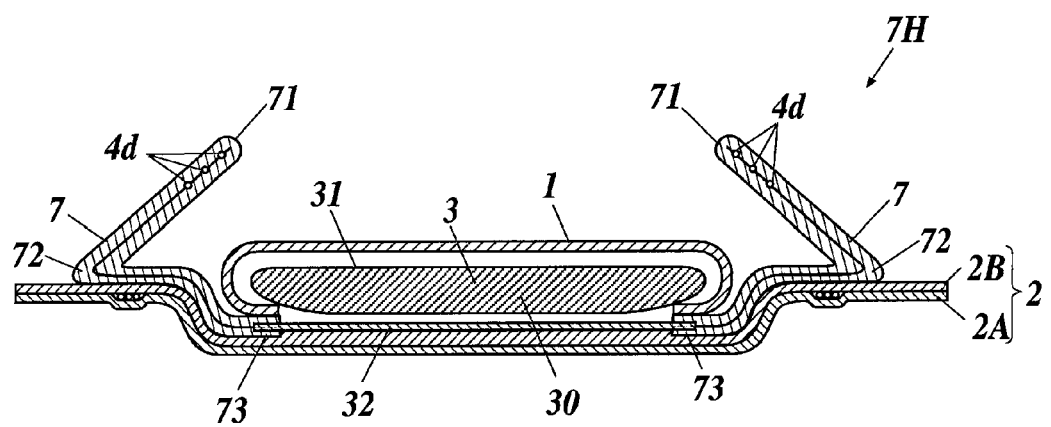
FIG. 2 This is a main part sectional view cut along a line II-II in the paper diaper 10 of FIG. 1.
Figure 3:
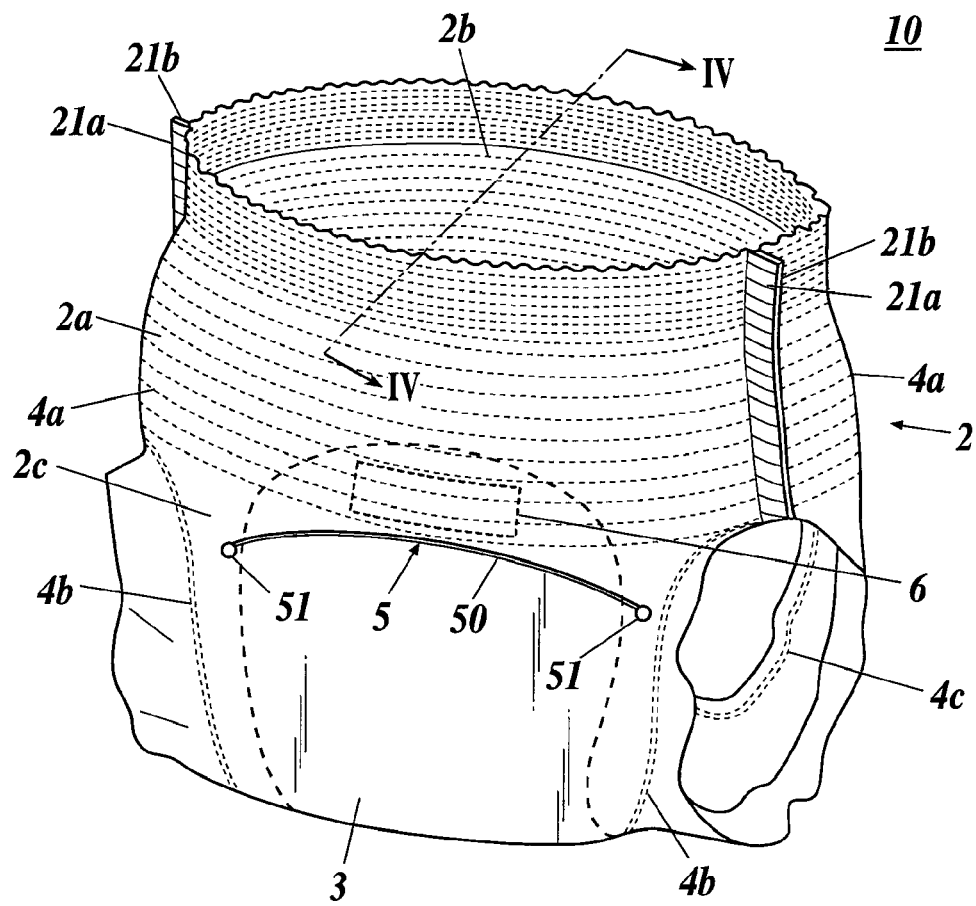
FIG. 3 This is a schematic view in which the paper diaper 10 of FIG. 1 is assembled.
Figure 4:
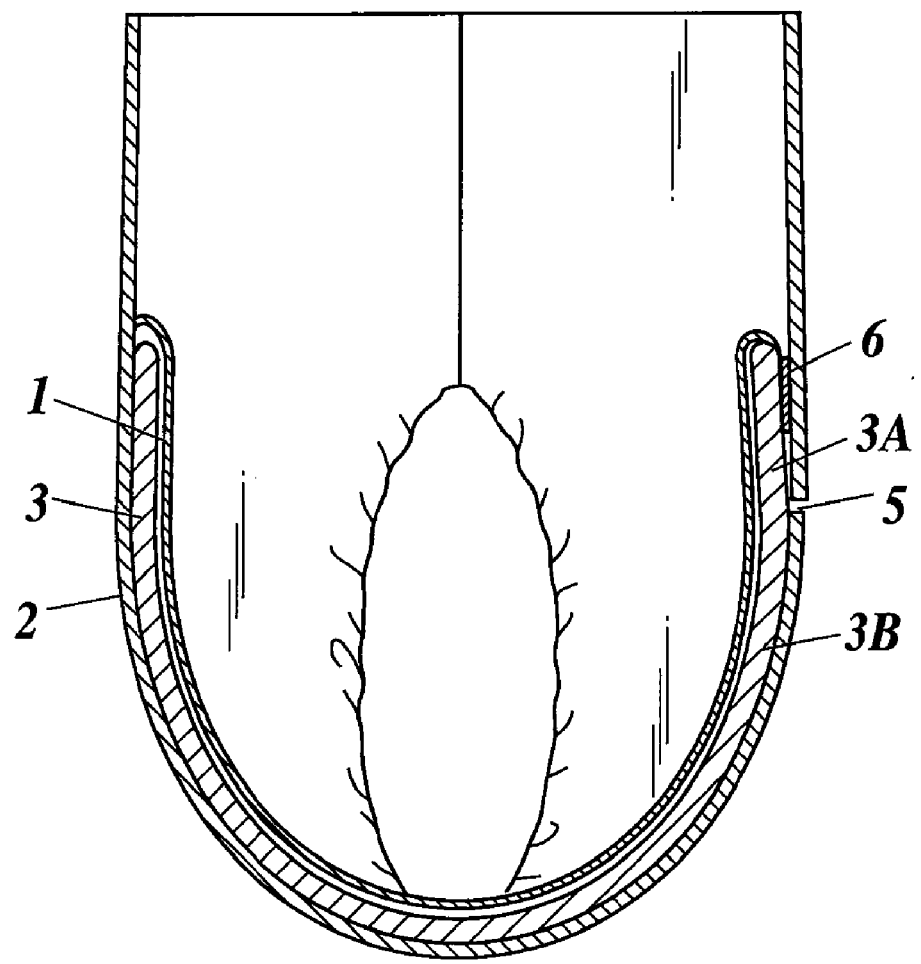
FIG. 4 This is a main part sectional view cut along a line IV-IV in the paper diaper 10 of FIG. 3.

Here, FIG. 1 is a developed view of the paper diaper which is exemplified as a preferred example of an absorbing article in which the present invention is applied. FIG. 2 is a main part sectional view of the paper diaper cut along the line II-II of FIG. 1. FIG. 3 is a schematic view in which the paper diaper is assembled and FIG. 4 is a main part sectional view of the paper diaper cut along a line IV-IV of FIG. 3.

As shown in FIGS. 1 and 2, the paper diaper 10 includes a liquid-permeable topsheet 1 which is positioned at a surface that contacts a human body, an external body 2 which is positioned outside when the paper diaper is used and worn and an absorbing body 3 which is positioned between the top sheet 1 and the external body 2.

For example, the top sheet 1 is formed of a liquid-permeable nonwoven fabric and is formed in a shape so as to cover the front surface (human body side) of the absorber.

The external body 2 is constituted of an external sheet 2A formed of a nonwoven fabric and an inner sheet 2B which is pasted on the external sheet 2A, and the external body 2 is formed in a shape so as to cover the back surface (outside when worn) of the absorbing body 3.

As for the nonwoven fabric material for forming the topsheet 1, the external sheet 2A, the after-mentioned gather sheet 7 and the like, both of natural fiber and synthetic fiber may be used. As for examples of natural fiber, cotton, cellulose (wood pulp), wool, silk and the like are suggested. Further, as for synthetic fiber, polypropylene (PP), polyethylene (PE), nylon, polyester (PET), acryl and the like are suggested, and a nonwoven fabric of PE/PP mixed, a nonwoven fabric of PE/PET mixed and a bicomponent fiber (mixed fiber) in which the above materials are arbitrarily combined may be used.

Moreover, as for a method for manufacturing a nonwoven fabric from the above fibrous materials, a well known method can be arbitrarily used. For example, any of the chemical bonding, thermal bonding, spunlace and the like may be used, and further with regards to synthetic fiber and the like, the spunbond method, the melt-blowing or a combination of the spunbond method and the above adhesion methods and the melt-blowing and the above adhesion methods and the like may be used. That is, any of the above methods can be used to manufacture the nonwoven fabric.

At one of the end portions of the external body 2, a ventral portion 2a which covers the front waist of a wearer of the paper diaper 10 is formed, and at the other of the end portions, a dorsal portion 2b which covers the back waist of a wearer is formed. In addition, in between the ventral portion 2a and the dorsal portion 2b, a crotch portion 2c which covers the crotch of a wearer is formed. The ventral portion 2a and the dorsal portion 2b are formed in an approximately rectangular shape having approximately equal widths.

Further, as shown in FIG. 3, by forming side portions by each of the edge portions 21a and 21a in the width direction of the ventral portion 2a and each of the edge portions 21b and 21b in the width direction of the dorsal portion 2b being respectively fixed to each other, the paper diaper 10 is to be formed in a shape of pants.

Moreover, between the external sheet 2A and the internal sheet 2B in the ventral portion 2a and in the dorsal portion 2b, a plurality of rubber threads 4a . . . as elastic member are provided and fixed so as to be sandwiched along the longitudinal direction having a predetermined space between each other, each of the plurality of rubber threads 4a being approximately parallel to each other in the width direction across the edge portions 21a and 21a and across the edge portions 21b and 21b. By the rubber threads 4a, the paper diaper 10 is structured so as to be stretchable at the body circumference and the waist circumference of a wearer when the paper diaper 10 is used.

Further, at the crotch portions 2c of the external sheet 2A and the internal sheet 2B, a plurality of rubber threads 4b are provided and fixed from one of the edge portions 21a of the ventral portion 2a curving along the shape of one of the edge portions 21c of the crotch portion 2c and across approximately center in the width direction to the other of the edge portions 21a of the ventral portion 2a curving along the shape of the other of the edge portions 21c of the crotch portion 2c. Furthermore, a plurality of rubber threads 4c are provided and fixed from one of the edge portions 21b of the dorsal portion 2b curving along the shape of one of the edge portions 21c of the crotch portion 2c and crossing approximately center in the width direction to the other of the edge portions 21b of the dorsal portion 2b curving along the shape of the other of the edge portions 21b of the crotch portion 2c. The rubber threads 4b and 4c are structured so that the external body 2 can fit the crotch and groin of a wearer when the paper diaper 10 is used.

Below the ventral portion 2a, there is provided a cut 50 along the width direction of the external body 2 and there is provided an opening 5 which opens by pulling the upper part and the lower part of the cut 50 in a direction separating from each other. For example, the cut 50 is in a curved shape that convexes upward apexing at the center thereof.

Moreover, the opening 5 has holes 51 and 51 which are provided continuously from both ends of the cut 50.

Here, the part where the opening 5 is to be formed in the external body 2 may be thickened by adhering a protection sheet for increasing strength. This is to prevent the holes 51 and 51 from being ripped by the stress applied when opening the opening 5.

For example, the absorbing body 3 absorbs aqueous component such as urine and the like as body fluid when the paper diaper 10 is used, and the absorbing body 3 is structured with an absorber 30 which is formed by an absorbent material such as cotton, pulp and the like, a sheet-type base material such as fiber, film and the like and a high water absorption resin being combined, a liquid-permeable crepe paper 31 which covers the absorber 30 and a water-proof film 32.

For example, the absorbing body 3 is formed in a sand clock shape so as to be worn at a position covering from the front body circumference of a human body, between the legs and to the back body circumference, wherein the width across both edge portions of crotch at the crotch portion 2c is set to short scale and the length from the ventral edge portion 3a which is the front body circumference to the dorsal edge portion 3b which is the back body circumference is set to long scale.

The crepe paper 31 is a liquid-permeable sheet and encloses the absorber 30 as a whole and functions to absorb body fluid.

The water-proof film 32 has a water-shielding property and functions to prevent the aqueous compound which passed through the crepe paper 31 from leaking in the external body 2 side.

The absorbing body 3 is positioned along the longitudinal direction of the external body 2 from the dorsal portion 2b of the external body 2 via the crotch portion 2c going over the opening 5 to the ventral portion 2a. Here, the portion of the absorbing body 3 in the crotch portion 2c side (below) than the opening 5 is an adhering portion 3B which is adhered to the external body 2 and the portion of the absorbing body 3 in the ventral portion 2a side (upper) than the opening 5 is a non-adhering portion 3A which is not adhered to the external body 2.

The adhering portion 3B is a region for applying adhesive for attaching the absorbing body 3 to the external body 2. In particular, the adhering portion 3B may be provided to either one of the external body 2 side or the absorbent main body 3 side.

As for the adhesion method, adhesion is generally carried out by hot-melt method. However, the adhesion may be carried out by any other methods.

Further, as for the adhesive applying pattern when using hot-melt method, the adhesive is generally applied entirely in the adhesive applying region. However, the adhesive may be applied in straight lines or in curved lines in the adhesive applying region.

In the back side (the external body 2 side) of the non-adhering portion 3A, a fastening unit 6 for detachably fastening the absorbing body 3 and the external body 2 is provided. As for the fastening unit 6, a mechanical tape, a sticky tape and the like can be used preferably.

The width of the non-adhering portion 3A is formed so as to be narrower than the width of the opening 5. Further, the end portion of the non-adhering portion 3A is formed in an arc shape.

Figure 6:
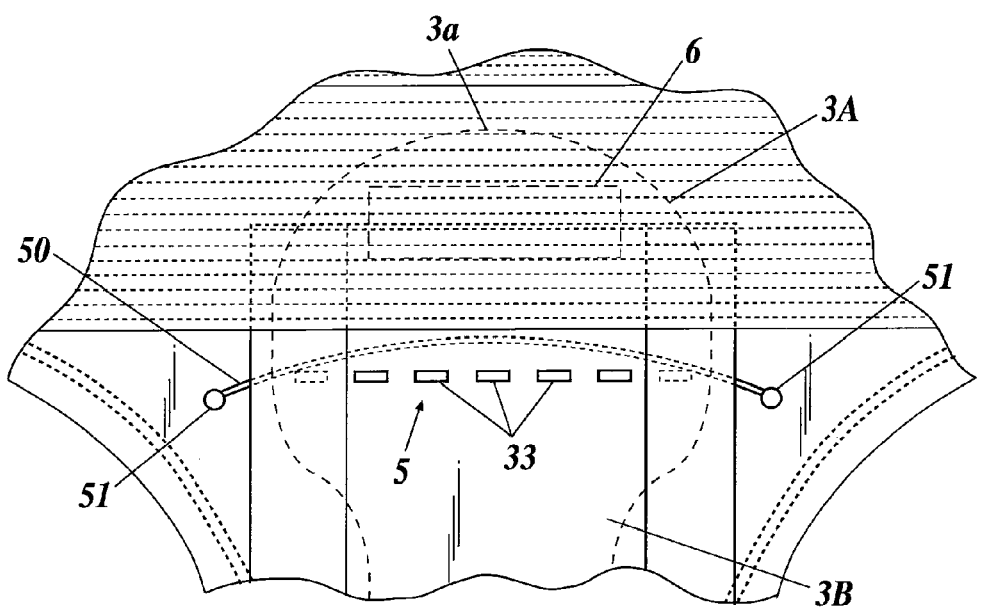
FIG. 6 This is an enlarged view for showing a main part structure of the non-adhering portion 3A of the absorbing body 3.

Further, as shown in FIG. 6, an embossing of plurality of embosses 33 . . . which continue along the width direction is carried out on font side (the top sheet 1 side) of the absorbing body 3 at the boundary portion of the adhering portion 3B and the non-adhering portion 3A.

In particular, the embosses 33 . . . of the embossing are formed in proximity of the opening 5 in a rectangular shape in which the width direction has long scale in plan view. Here, shape of the emboss is not particularly limited and may be in any shape such as circle, oval and the like.

At the both edge portions in the width direction of the absorbing body 3, in the topsheet 1 side of the paper diaper 10, there is respectively provided gather sheets 7 and 7 at the positions corresponding to both of the crotch edge portions 3c from the ventral edge portion 3a to the dorsal edge portion 3b of the absorber 30.

These gather sheets 7 and 7 are formed by folding liquid-permeable nonwoven fabric sheets in half and by adhering the inside faces thereof by hot-melt method, heat-seal method, ultrasonic sealing and the like.

Here, as shown in FIG. 2, the folded side end portions of the nonwoven fabrics which are folded in half are made to be free end portions 71, origins of the three-dimensional risings are made to be rising portions 72, and the end portions which are to be fixed to the external body 2 side are made to be fixing end portions 73. By the fixing end portions 73 being adhered so as to be sandwiched by the topsheet 1 and the external sheet 2A, each of the gather sheets 7 and 7 is fixed. Further, a plurality of rubber threads 4d are sandwiched and adhered between the inner faces of the nonwoven fabrics which are folded in half.

In a state where the gather sheets 7 and 7 are adhered to the paper diaper 10, the three-dimensional gathers 7H are formed by the free end portions 71 which are the fore-end portions being raised. Further, the gather sheets 7 are structured so as to be deformed by stretching freely according to the body shape of a wearer and so as to easily fit the wearer by the rubber threads 4.

Next, the operation of the embodiment will be described.

At the time when the paper diaper 10 is worn, the absorbing body 3 and the external body 2 are fastened by the fastening unit 6 and the opening 5 maintains a closed state. Further, even when the paper diaper 10 sags downward when urination is carried out in the absorbing body 3, the opening 5 maintains the closed state because the absorbing body 3 and the external body 2 are fastened by the fastening unit 6 (see FIG. 4).

On the other hand, when urination is to be carried out toward outside by taking out the male genitalia from the opening 5 while wearing the paper diaper 10, the absorbing body 3 and the external body 2 are to be separated from each other and the opening 5 opens due to releasing the fastened state of the absorbing body 3 and the external body 2 by the fastening unit 6, and the male genitalia can be taken outside.

Figure 5:
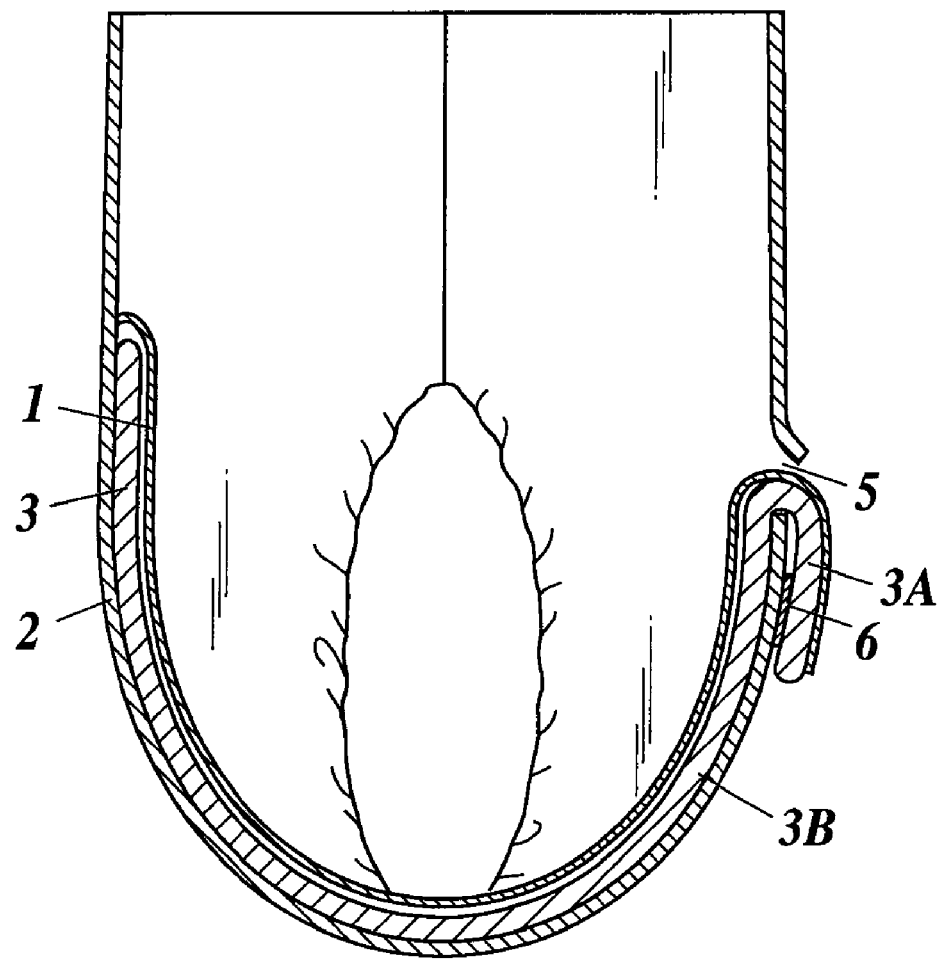
FIG. 5 This is a diagram for showing a state where the non-adhering portion 3A of the absorbing body 3 is taken out.

At this time, the absorbing body 3 is positioned from below to above the opening 5 so as to go over the opening 5 and the portion of the absorbing body 3 which positions above the opening 5 is made to be a non-adhering portion 3A. Therefore, the non-adhering portion 3A of the absorbing body 3 can be taken outside along with the male genitalia (see FIG. 5).

Further, the non-adhering portion 3A which is taken out can be fastened to outside of the external body 2 by the fastening unit 6.

At this time, width of the non-adhering portion 3A is formed so as to be narrower than width of the opening 5. Therefore, the non-adhering portion 3A can be taken out from the opening 5 easily.

As described above, according to the embodiment, the opening 5 can be prevented from being opened due to the paper diaper 10 sagging downward as a whole by the weight of urine when urination is carried out in the absorbing body 3 because the upper part of the opening 5 can be fastened by the fastening unit 6.

Moreover, when urination is carried out by taking male genitalia out from the opening 5, the non-adhering portion 3A of the absorbent main body 3 can be taken out along with the male genitalia and residual urine can be caught by the non-adhering portion 3A. Therefore, urine can be prevented from attaching to the main body of the paper diaper 10.

Further, when urination is carried out by taking male genitalia out from the opening 5, the opening 5 can maintain the opened state by fastening the fastening unit 6 to outside of the external body 2. Therefore, urination can be carried out easily by one hand and this is convenient for the wearer.

Furthermore, the opening 5 is formed in a curved shape convexing upward. Therefore, center of the opening 5 is easy to open and male genitalia can be taken out easily, and this is convenient for the wearer.

Moreover, the end portion of the non-adhering portion 3A of the absorbing body 3 is formed in an arc shape. Therefore, left end and right end portions of the non-adhering portion 3A will not be caught when taking it out from the opening 5 and the non-adhering portion 3A can be taken out from the opening 5 easily, and this is convenient for the wearer.

Further, the opening 5 includes holes 51 and 51 at both ends of the cut 50. Therefore, the stress applied to both ends of the cut 50 when the opening 5 opens is dispersed and the both ends of the cut 50 can be prevented from being ripped.

Furthermore, the width of the non-adhering portion 3A of the absorbing body 3 is narrower than the width of the opening 5. Therefore, it is easy to pull out the non-adhering portion 3A from the opening 5 and this is convenient for the wearer.

Moreover, the shape of the end portion of the non-adhering portion 3A is an arch shape. Therefore, it is easy to pull out the non-adhering portion 3A from the opening 5 and this is convenient for the wearer.

Moreover, at the boundary of the adhering portion 3B and the non-adhering portion 3A of the absorbing body 3, embossing is carried out. Therefore, the absorbing body 3 can be folded easily when taking the non-adhering portion 3A outside and the fastening unit 6 can be fastened to outside of the external body 2 easily. Further, the embossing can prevent urine from dispersing to the non-adhering portion 3A.

Here, in the embodiment, embossing is carried out along width direction at the boundary of the adhering portion 3B and the non-adhering portion 3A. However, alternatively, a slit can be formed along the width direction of the absorbing body 3, for example. In such structure, the absorbing body 3 is also easy to fold when taking the non-adhering portion 3A outside, and the fastening unit 6 can be fastened to outside of the external body 2 easily.

Moreover, embossing is carried out at the boundary of the adhering portion 3B and the non-adhering portion 3A on the back side (the topsheet 1 side) of the absorbing body 3. However, the embossing may be carried out on the front side (the external body 2 side) of the absorbing body 3. Even when the embossing is carried out in such way, the absorbing body 3 can be made to be folded easily when taking the non-adhering portion 3A outside.

Further, embossing may be carried out on both sides which are the back side (the topsheet 1 side) and the front side (the external body 2 side) of the absorbing body 3.

Furthermore, in the embodiment, the width of the non-adhering portion 3A is made to be narrower than the width of the opening 5. However, width of the non-adhering portion 3A may be formed to be wider than the opening 5. In such case, when urination is to be carried out outward, male genitalia may be taken out from the opening 5 by folding the non-adhering portion 3A inward of the paper diaper 10.

Other than the above, it is needless to say that the present invention is not limited to the above embodiment and can be changed arbitrarily.

Embodiment 2

Next, embodiment 2 of the present invention will be described mainly for the aspects different from embodiment 1, and the same symbols are used for the parts same as that of embodiment 1 and the descriptions will be omitted.

Figure 7:
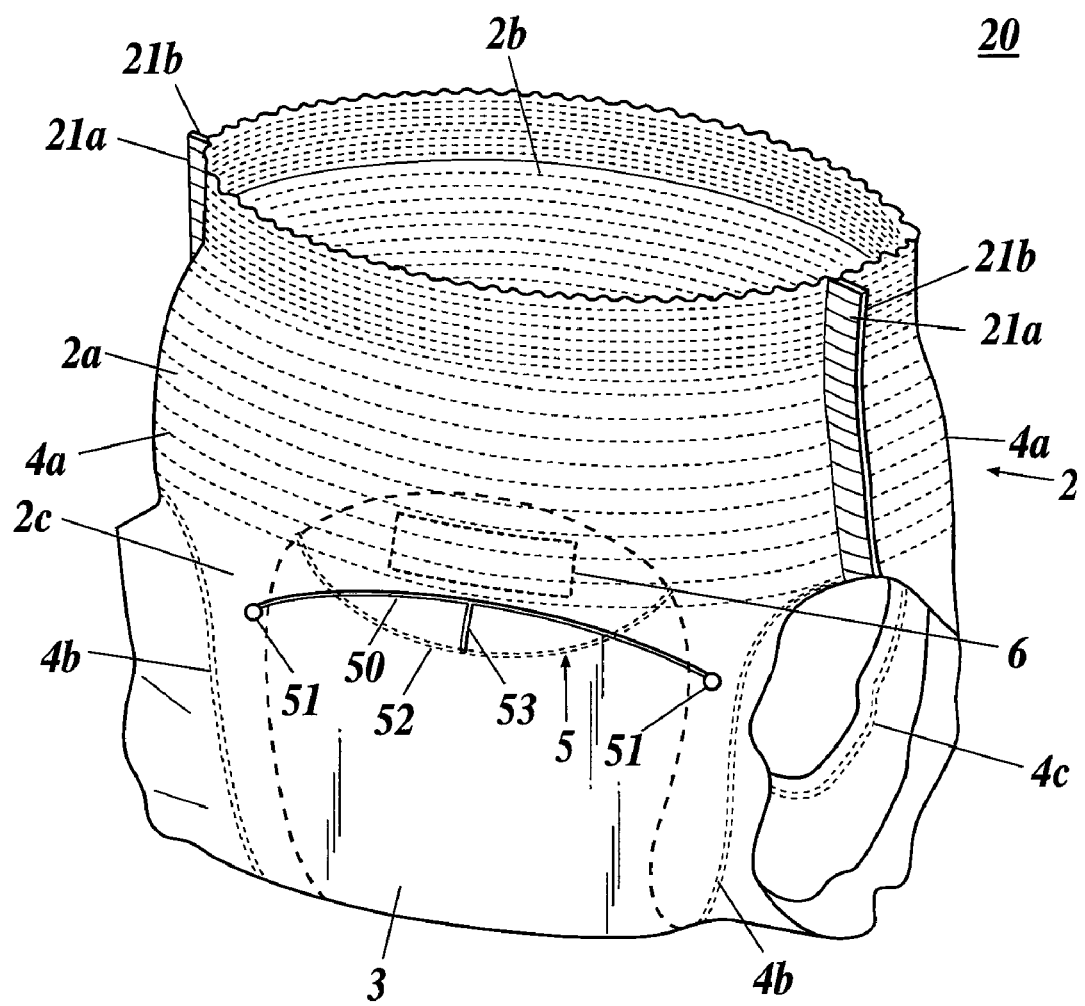
FIG. 7 This is a developed view of the paper diaper 20 of embodiment 2 in which the absorbing article of the present invention is applied.

FIG. 7 is a schematic diagram when the paper diaper 20 according to embodiment 2 is assembled.

As shown in FIG. 7, in the paper diaper 20 of embodiment 2, an elastic body 52 to which a biasing force in a closing direction of the opening 5 is given is provided in proximity of the opening 5.

In particular, the elastic body 52 has a curved shape convexed downward apexing at center thereof in a state where tension is given and is adhered between the external sheet 2A and the inner sheet 2B so as to go over the opening 5.

By having such structure, there is a biasing force that pulls both ends of the opening 5 upward. Therefore, the closed state of the opening 5 can be maintained easily.

Moreover, by disposing the elastic body 52 so as to go over the opening 5, both ends of the opening 5 can be made not to be ripped easily.

Further, when the elastic body 52 is disposed along the opening 5, the elastic body 52 contracts and bends, and therefore the opening 5 can be pulled by a finger easily when opening and the opening 5 opens easily. Thus, male genitalia can be taken out easily.

Furthermore, the opening 5 includes a second cut 53 which is formed so as to be orthogonal to the cut 50, downward from the center of the cut 50.

By having such structure, the opening 5 is easier to broaden when opening the opening 5. Therefore, the non-adhering portion 3A of the absorbing body 3 and male genitalia can be taken out easily.

Further, in the above case, by forming the second cut 53 on the trace of the elastic body 52, the cut 50 and the second cut 53 do not separate from each other and the shape can be maintained.

Embodiment 3

Next, embodiment 3 of the present invention will be described mainly for the aspects different from embodiment 1, and the same symbols are used for the parts same as that of embodiment 1 and the descriptions will be omitted.

Figure 8:
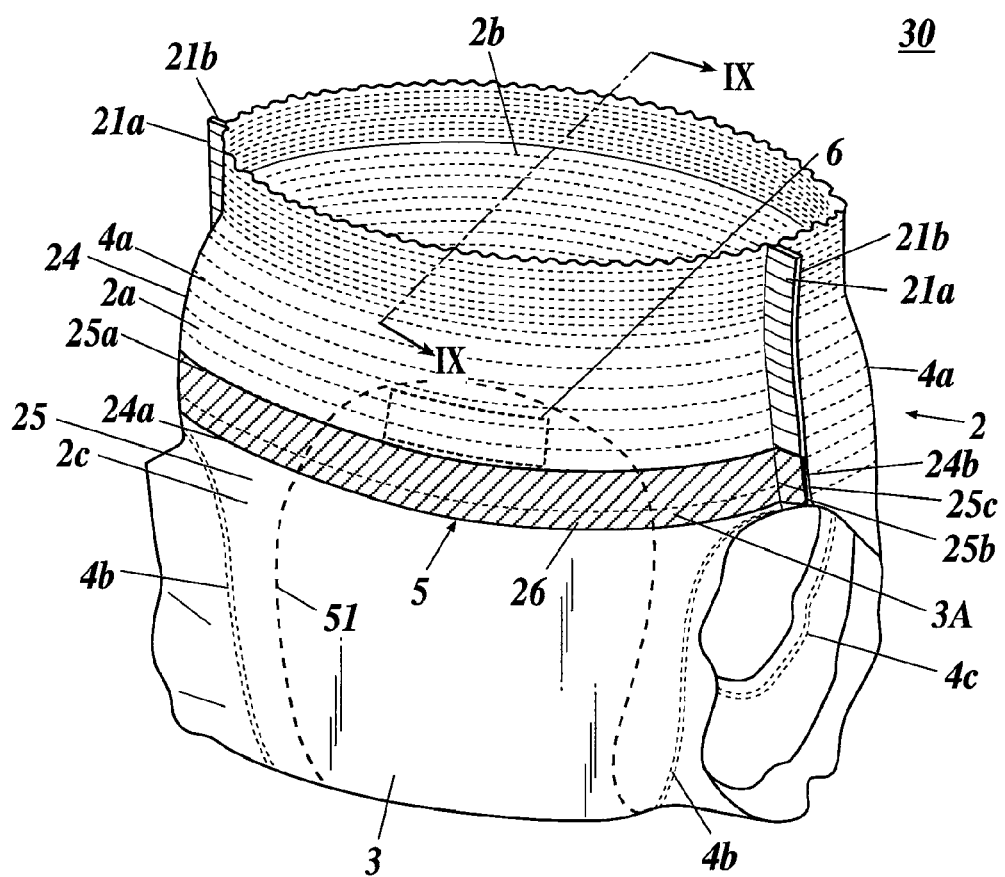
FIG. 8 This is a developed view of the paper diaper 30 of embodiment 3 in which the absorbing article of the present invention is applied.
Figure 9:
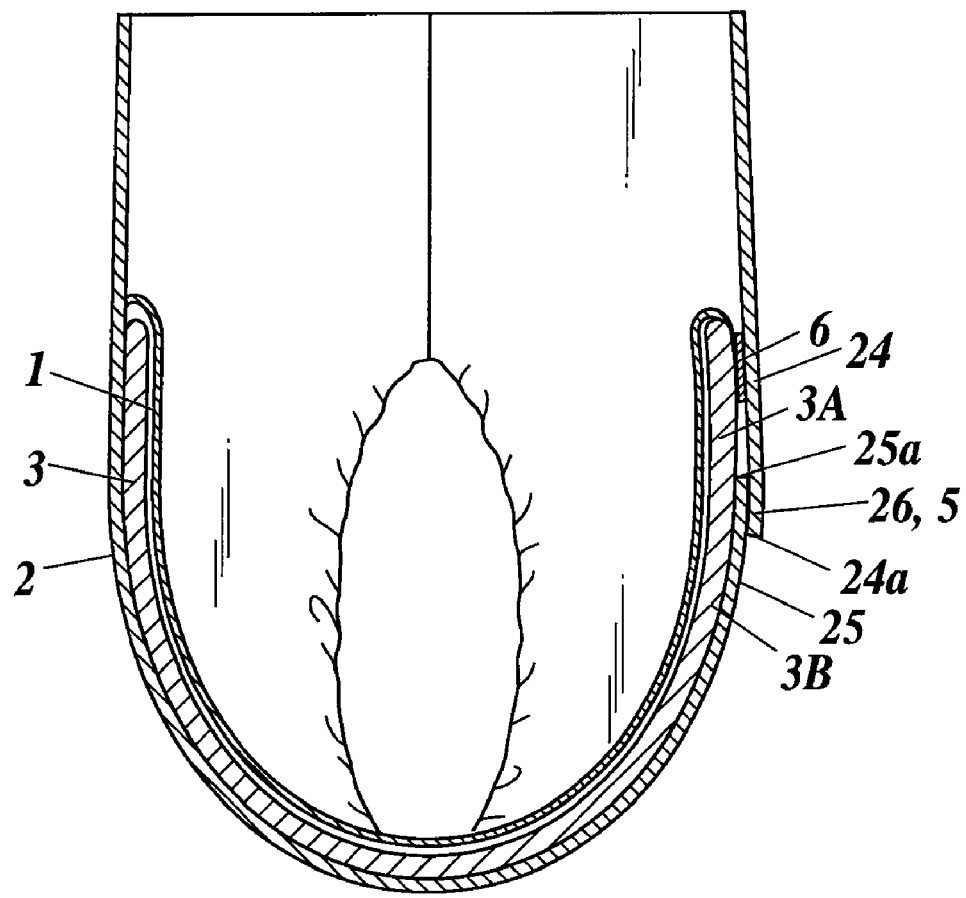
FIG. 9 This is a main part sectional view cut along a line IX-IX in the paper diaper 30 of FIG. 8.

FIG. 8 is a schematic diagram in which the paper diaper 30 according to embodiment 3 is assembled, and FIG. 9 is a main part sectional diagram cut along the line IX-IX of the paper diaper 30 shown in FIG. 8.

As shown in FIG. 8, in the paper diaper 30 of embodiment 3, the external body 2 is structured with an upper sheet 24 which forms the ventral portion 2a and a lower sheet 25 which forms the dorsal portion 2b and the crotch portion 2c. Further, the opening 5 is formed with a lower end portion 24a of the upper sheet 24 and an upper end portion 25a of the lower sheet 25.

In particular, the lower end portion 24a of the upper sheet 24 and the upper end portion 25a of the lower sheet 25 are overlapped so that the upper sheet 24 be outside. Both left and right end portion 24b and 24b of the upper sheet 24 and both left and right end portions 25b and 25b of the lower sheet 25 at the overlapped portion (hereinafter, called overlapping portion 26, see shaded area in FIG. 8) are respectively adhered to each of the end portions 25c and 25c in the width direction side of the dorsal portion 2b of the lower sheet 25 to form the side portions.

Further, center portion of the overlapping portion 26 is to open by pulling the lower end portion 24a of the upper sheet 24 and the upper end portion 25a of the lower sheet 25 in a direction so as to separate from each other, and thereby, the opening 5 is formed.

As shown in FIG. 9, the absorbing body 3 is positioned along the longitudinal direction from the crotch portion 2c to ventral portion 2a of the external body 2 so as to go over the opening 5, and the portion of the absorbing body 3 which is in upper side than the opening 5 is the non-adhering portion 3A. The fastening unit 6 is provided at the non-adhering portion 3A and the non-adhering portion 3A is fastened to the upper sheet 24 at the upper portion than the overlapping portion 26.

By having such structure, the opening 5 can be broadened easily when opening the openings. Therefore, the non-adhering portion 3A of the absorbing body 3 and male genitalia can be taken out easily.

Industrial Applicability

The present invention can be applied to manufacturing of absorbing articles and the like.

Description of Marks 1 topsheet
2 external body
2A external sheet
2B inner sheet
2a ventral portion
2b dorsal portion
2c crotch portion
24 upper sheet
25 lower sheet
3 absorbing body
30 absorber
31 crepe paper
32 water-proof film
3A non-adhering portion
3B adhering portion
4a, 4b, 4c rubber thread
5 opening
50 cut
51 hole
52 elastic body
53 second cut
6 fastening unit
7 gather sheet
71 free end portion
72 rising portion
73 fixing end portion
10 paper diaper

The invention claimed is:

1. A pants type absorbing article, comprising:
an absorbing body including an absorber;
a ventral portion;
a dorsal portion;
a crotch portion which is positioned between the ventral portion and the dorsal portion; and
an external body for adhesively securing the absorbing body to the crotch portion,
wherein:
the external body has a cut along a width direction below the ventral portion and comprises an opening which opens by pulling an upper part and a lower part of the cut so as to separate from each other,
the absorbing body is positioned along a longitudinal direction from the crotch portion to the ventral portion of the external body going over the opening,
a portion of the absorbing body below the opening forms an adhering portion where the absorbing body and the external body are adhered, and a portion of the absorbing body above the opening forms a non-adhering portion where the absorbing body and the external body are not adhered, and
the absorbing article comprises a fastening unit to detachably fasten the absorbing body and the external body at the non-adhering portion.

2. The absorbing article according to claim 1, wherein the cut has a curved shape convexing upward.

3. The absorbing article according to claim 1, wherein the opening comprises holes provided at both ends of the cut so as to continue from the cut.

4. The absorbing article according to claim 1, wherein the opening comprises a second cut which is formed to extend downward from a center of the cut so as to be orthogonal to the cut.

5. The absorbing article according to claim 1, wherein a width of the non-adhering portion of the absorbing body is narrower than a width of the opening.

6. The absorbing article according to claim 1, wherein an end portion of the non-adhering portion of the absorbing body is shaped in an arc shape.

7. The absorbing article according to claim 1, wherein at a boundary portion of the adhering portion and the non-adhering portion of the absorbing body, an embossing that continues along a width direction is carried out.

8. The absorbing article according to claim 1, wherein at a boundary portion of the adhering portion and the non-adhering portion of the absorbing body, a slit is formed along a width direction.

9. The absorbing article according to claim 1, wherein an elastic body in which a biasing force in a closing direction of the opening is given is provided in proximity to the opening.

10. A pants type absorbing article, comprising:
an absorbing body including an absorber;
a ventral portion;
a dorsal portion;
a crotch portion which is positioned between the ventral portion and the dorsal portion; and
an external body for adhesively securing the absorbing body to the crotch portion,
wherein:
the external body comprises an upper sheet for forming the ventral portion and a lower sheet for forming the dorsal portion and the crotch portion,
a lower end portion of the upper sheet and an upper end portion of the lower sheet are overlapped so that the upper sheet is outside and the overlapped portion forms an opening which opens by pulling the lower end portion of the upper sheet and the upper end portion of the lower sheet in so as to separate from each other,
the absorbing body is positioned along a longitudinal direction from the crotch portion to the ventral portion of the external body going over the opening, a portion of the absorbing body below the opening forms an adhering portion where the absorbing body and the external body are adhered, and a portion of the absorbing body above the opening forms a non-adhering portion where the absorbing body and the external body are not adhered, and the absorbing article comprises a fastening unit to detachably fasten the absorbing body and the external body at the non-adhering portion.

\* \* \* \* \*